United States Patent [19]
McGuire et al.

[11] Patent Number: 5,520,693
[45] Date of Patent: May 28, 1996

[54] FEMORAL GUIDE AND METHODS OF PRECISELY FORMING BONE TUNNELS IN CRUCIATE LIGAMENT RECONSTRUCTION OF THE KNEE

[76] Inventors: David A. McGuire, 408 Laurel St., Suite 202, Anchorage, Ak. 99508; Roger Paterson, 32 Payneham Rd., Stepney 5069, South Australia, Australia

[21] Appl. No.: 839,466

[22] Filed: Feb. 19, 1992

[51] Int. Cl.$^6$ .............................. A61F 5/00; A61B 17/58
[52] U.S. Cl. .................................. 606/86; 606/87; 606/88
[58] Field of Search .............................. 606/103, 86, 87, 606/88, 181, 222, 223, 96, 97, 98

[56] References Cited

U.S. PATENT DOCUMENTS

| | | | |
|---|---|---|---|
| 2,242,003 | 5/1941 | Lorenzo | 128/92 |
| 2,267,925 | 12/1941 | Johnston | 128/92 |

(List continued on next page.)

FOREIGN PATENT DOCUMENTS

| | | |
|---|---|---|
| 221356A1 | 4/1985 | European Pat. Off. . |
| 0240457 | 7/1987 | European Pat. Off. . |
| 0281763 | 9/1988 | European Pat. Off. . |
| 0384098 | 8/1990 | European Pat. Off. . |
| 0495487A2 | 1/1991 | European Pat. Off. . |

OTHER PUBLICATIONS

"A New Femoral Drill Guide for Athroscopically Assisted Anterior Cruciate Ligament Replacement", Howard J. Marans, et al., *Arthroscopy: The Journal of Arthroscopic and Related Surgery*, 8(2): 234–238, 1992.

McGinty; *Arthroscopic Surgery Update*, 1985, Techniques in Orthopaedics, vol. 5, pp. 72–77.

*Arthroscopic Technique for Anterior Cruciate Reconstruction*, by Acufex Microsurgical, Inc. 1988.

*Technique for Rear Entry ACL Guide*, by Acufex Microsurgical, Inc. 1988.

Lambert, K.; *Vascularized Patellar Tendon Graft with Rigid Internal Fixation for Anterior Cruciate Ligament Insufficiency*, Jul. 1982, pp. 85–89.

Kariya and Kurosawa; "Arthroscopically Aided Anterior Cruciate Ligament Reconstruction Using a New Drill Wire Guide", 1989, *The Journal of Arthroscopic and Related Surgery*, vol. 5, No. 3, pp. 227–231.

Hanson and Frost; "A Simple Suture Passer for Use in Cruciate Ligament Repair in the Knee", 1977, *Clinical Orthopaedics and Related Research*, pp. 45–46.

(List continued on next page.)

*Primary Examiner*—Michael A. Brown
*Attorney, Agent, or Firm*—Bromberg & Sunstein

[57] ABSTRACT

A femoral guide for precisely positioning a guide wire on a bone surface of the femur includes a body having a lumen for receiving a guide wire and a tongue protruding from the body for engaging an edge or reference point on the bone surface with the tongue being spaced a predetermined distance from a longitudinal axis of the lumen. The lumen includes an opening allowing a guide wire extending through the lumen to contact the bone surface at a location spaced from the edge substantially the predetermined distance with the tongue engaging the edge. A stylus on the body can be driven into the bone to secure and stabilize the femoral guide prior to driving the guide wire into the bone through the lumen. With the guide wire driven into the bone, a bone tunnel can be formed substantially concentrically or coaxially along the guide wire such that a longitudinal axis of the bone tunnel will be disposed from the edge substantially the predetermined distance. Methods of precisely forming bone tunnels include the steps of engaging an edge of a bone surface with a tongue of the femoral guide, inserting a guide wire through a lumen of the femoral guide, driving the guide wire into the bone through the lumen and forming a bone tunnel in the bone along the guide wire such that a longitudinal axis of the bone tunnel will be disposed from the edge engaged by the tongue a distance substantially equal to the distance that the tongue is disposed from a longitudinal axis of the lumen.

12 Claims, 3 Drawing Sheets

U.S. PATENT DOCUMENTS

| | | | |
|---|---|---|---|
| 2,301,500 | 11/1942 | Anderson | 606/103 |
| 2,697,433 | 12/1954 | Zehnder | 606/103 |
| 4,273,117 | 6/1981 | Neuhauser | 128/92 |
| 4,381,770 | 5/1983 | Neufeld | 128/92 |
| 4,383,527 | 5/1983 | Asnis et al. | 128/92 EB |
| 4,450,835 | 5/1984 | Asnis et al. | 128/92 EB |
| 4,535,768 | 8/1985 | Hourahane et al. | 128/305.1 |
| 4,625,717 | 12/1986 | Covitz | 606/103 |
| 4,667,664 | 5/1987 | Taylor et al. | 128/92 VV |
| 4,686,972 | 8/1987 | Kurland | 128/92 |
| 4,712,542 | 12/1987 | Daniel et al. | 128/92 V |
| 4,721,116 | 1/1988 | Schintgen et al. | |
| 4,738,255 | 4/1988 | Goble | |
| 4,739,751 | 4/1988 | Sapega et al. | |
| 4,773,417 | 9/1988 | Moore et al. | 128/303 R |
| 4,781,182 | 11/1988 | Purnell et al. | 128/92 VD |
| 4,784,126 | 11/1988 | Hourahane et al. | 128/92 YF |
| 4,787,377 | 11/1988 | Laboreau | 128/92 VD |
| 4,823,780 | 4/1989 | Odensten et al. | 128/92 VD |
| 4,883,048 | 11/1989 | Purnell et al. | 128/92 VD |
| 4,901,711 | 2/1990 | Goble et al. | 606/98 |
| 4,920,958 | 5/1990 | Walt et al. | 606/96 |
| 4,927,421 | 5/1990 | Goble et al. | 606/73 |
| 4,950,270 | 8/1990 | Bowman et al. | 606/72 |
| 4,964,861 | 10/1990 | Agee | 606/87 |
| 4,969,895 | 11/1990 | McLeod et al. | 606/96 |
| 5,002,545 | 3/1991 | Whiteside et al. | 606/80 |
| 5,057,113 | 10/1991 | Mingozzi | 606/103 |
| 5,112,335 | 5/1992 | Laboureau | 606/88 |
| 5,112,337 | 5/1992 | Paulos et al. | 606/96 |
| 5,139,520 | 8/1992 | Rosenberg | 623/13 |
| 5,147,367 | 9/1992 | Ellis | 606/96 |
| 5,152,763 | 10/1992 | Johnson | 606/86 |
| 5,152,766 | 10/1992 | Kirkley | 606/103 |
| 5,154,720 | 10/1992 | Trott et al. | 606/96 |
| 5,320,115 | 6/1994 | Kenna | 623/13 |
| 5,320,626 | 6/1994 | Schmieding | |

OTHER PUBLICATIONS

Odensten and Gillquist; "A Modified Technique for Anterior Cruciate Ligament (ACL) Surgery Using a New Drill Guide for Isometric Positioning of the ACL", 1976, *Clinical orthopaedics and Related Research*, pp. 154–158.

Beyer; "A Unitunnel Technique for Athroscopic Anterior Cruciate Ligament Reconstruction", 1988, *Bulletin of the Hospital for Joint Diseases Orthopaedic Institute*, vol. 48, No. 2, pp. 164–169.

Burnett and Fowler; "Reconstruction of the Anterior Cruciate Ligament: Historical Overview", Jan. 1985, *Orthopedic Clinics of North America*, vol. 16, No. 1, pp. 143–157.

Raunest; "Application of a New Positioning Device for Isometric Replacement in Anterior Cruciate Ligament Repair and Reconstruction", Feb. 1991, *The Journal of Trauma*, vol. 31, No. 2, pp. 223–229.

Matthews, Martin and Wolock; "Accurate Tunnel Placement Using Drill Guides in Knee Ligament Reconstruction", Dec. 1, 1989, *Orthopaedic Review*, vol. XIX, No. 9, pp. 822–824.

Bassi and Fioriti; "A New Guide in the Surgical Reconstruction of the Cruciate Ligaments", Jun. 1990, *Italian Journal of Orthopaedics and Traumatology*, pp. 215–219.

Penner, Darrell A., M.D. et al.; "An in vitro study of anterior cruciate ligament graft placement and isometry", *The American Journal of Sports Medicine*, vol. 16, No. 3, 1988.

Melhorn, J. Mark, M.D.; "The relationship of the femoral attachment site to the isometric tracking of the anterior cruciate ligament graft", *The American Journal of Sports Medicine*, vol. 15, No. 6, 1987.

Bylski–Austrow, D. I. et al.; "Anterior Cruciate Ligament Replacements: A Mechanical Study of Femoral Attachment Location, Flexion Angle at Tensioning, and Initial Tension", *Journal of Orthopaedic Research*, 8:522–531, 1990.

Hefzy, Mohamed S., Ph.D. et al.; "Factors affecting the region of most isometric femoral attachments Part II: The anterior cruciate ligament", *The American Journal of Sports Medicine*, vol. 17, No. 2, 1989.

Odensten, Magnus, M.D., Ph.D. et al.; "Functional Anatomy of the Anterior Cruciate Ligament and a Rationale for Reconstruction", *Sports and Trauma Research Group*, vol. 67–A, No. 2, Feb. 1985.

FEMORAL GUIDE AND METHODS OF PRECISELY FORMING BONE TUNNELS IN CRUCIATE LIGAMENT RECONSTRUCTION OF THE KNEE

BACKGROUND OF THE INVENTION

1. Field of the Invention

The present invention pertains to surgical instruments for precisely positioning guide wires in bone allowing tunnels to be formed in the bone along the guide wires and, more particularly, to femoral guides for precisely positioning guide wires in the femur in cruciate ligament reconstruction of the knee allowing bone tunnels to be formed in the femur along the guide wires at sites anatomically equivalent to the cruciate ligament and to methods of precisely forming bone tunnels.

2. Description of the Prior Art

Various surgical procedures utilize graft or prosthetic ligaments to reconstruct natural ligaments that have been damaged by injury or disease. Where the ligaments to be reconstructed are found in joints or articulations of the body, i.e., the connections of the various surfaces of the bones in the body, graft or prosthetic ligaments are typically implanted and fixated in bones of the joint at sites anatomically equivalent to the natural ligament. In cruciate ligament reconstruction, such as anterior cruciate ligament reconstruction of the knee, tandem, isometrically positioned bone tunnels are formed, respectively, in the tibia and femur at sites anatomically equivalent to attachment of the anterior cruciate ligament, and a graft or prosthetic ligament having bone blocks at its ends is inserted in the bone tunnels to extend across the knee joint with the bone blocks disposed, respectively, in the bone tunnels. Interference bone fixation screws are inserted in the tibial and femoral bone tunnels to be positioned laterally between the bone blocks and walls of the bone tunnels to fixate the ligament and provide a bone-tendon-bone graft. In anterior cruciate ligament reconstruction of the knee, it is very important that the bone tunnels be located at the anatomic sites of attachment of the anterior cruciate ligament; and, where anterior cruciate ligament reconstruction is performed as an open surgical procedure utilizing relatively long incisions on the order of ten inches in length to access the knee joint, the increased room for maneuverability afforded by the long incisions can enhance proper placement of the tibial and femoral bone tunnels. However, open surgery possesses numerous disadvantages over closed, or least invasive surgery, including increased invasiveness and trauma, prolonged hospitalization and rehabilitation times, increased patient discomfort, possible violation of capsular mechanoreceptors, dessication of articular cartilage and delayed post-surgical mobility. Accordingly, it is preferred to perform anterior cruciate ligament reconstruction as a least invasive, closed, or endoscopic, procedure wherein portals of minimal size, such as are formed with a puncture or stab wound, in tissue adjacent the knee are utilized to access the knee joint with the knee being visualized with an arthroscope, the portals being just large enough to accommodate surgical instruments inserted at the knee joint. Arthroscopic anterior cruciate ligament reconstruction provides numerous benefits over open surgery including minimal invasiveness and trauma, performance on an out-patient basis, reduced rehabilitation time, decreased patient discomfort, early, aggressive range of motion, cosmetically pleasing incisions, completion with tourniquet times under one hour, the opportunity to perform a diagnostic arthroscopy without having to commit to anterior cruciate ligament reconstruction unless confirmed by the diagnostic findings and early weight bearing without loss of fixation.

Where cruciate ligament reconstruction is performed as a closed, or endoscopic, surgical procedure, the small size of the portals limits access to and maneuverability at the knee joint making it relatively more difficult to precisely place the tibial and femoral bone tunnels at sites anatomically equivalent to the cruciate ligament. In most cases, guide wires or pins are inserted through arthroscopic size portals from externally of the body and are driven, from externally of the body, in the tibia and femur at desired locations for longitudinal axes, or centers, of the tibial and femoral bone tunnels, allowing the bone tunnels to be formed along the guide wires, such as by drilling or reaming, substantially coaxially or concentrically with the guide wires. Although the guide wires are effective in guiding instruments, such as drills and reamers, utilized to form the bone tunnels, problems can arise in arthroscopic cruciate ligament reconstruction in precisely positioning or locating the guide wires. If the guide wires are not located and inserted at sites anatomically equivalent to attachment of the cruciate ligament, the tibial and femoral bone tunnels, as guided by the guide wires, will not be properly located, and ligament reconstruction will be impaired. In arthroscopic anterior cruciate ligament reconstruction, it is difficult to position a guide wire on the femur at a position corresponding to the anatomic center of attachment of the anterior cruciate ligament. In order to position a tip of the guide wire on the femoral condyle at the anatomic center for the anterior cruciate ligament and drive the guide wire into the femur such that a bone tunnel formed along the guide wire will have a longitudinal axis substantially aligned with the anatomic center of the anterior cruciate ligament, the guide wire must be inserted through a tibial bone tunnel from a portal of minimal size, and a tip of the guide wire must be located on the femoral condyle with the guide wire held and driven into the femur from externally of the knee. When positioning the tip of the guide wire on the femoral condyle, it is desired that the tip be positioned high in a notch on the femoral condyle, the notch being formed in a notchplasty procedure prior to formation of the bone tunnels, such that the longitudinal axis of the femoral bone tunnel will be disposed sufficiently anterior, i.e., approximately 6–7 millimeters, to the posterior edge or "over-the-top ridge" of the notch and the femoral bone tunnel will be as far posterior as possible while still allowing a tunnel and not a trough with the cortical margin of the femur being neither too wide nor too narrow. However, it is extremely difficult in arthroscopic anterior cruciate ligament reconstruction to position and hold the guide wire from externally of the knee such that the tip of the guide wire is optimally, isometrically positioned on the femur; and, even when properly positioned, the guide wire can slip or shift prior to being driven into the femur resulting in an improperly positioned femoral bone tunnel and impaired placement of the graft or prosthetic ligament. Where instruments are used to help guide or hold the guide wire, the instruments themselves can slip or shift causing displacement of the guide wire; and, frequently, the use of instruments does not eliminate the need for a surgeon to estimate where to place instruments such as drills or reamers when forming the femoral bone tunnel along the guide wire. Accordingly, arthroscopic anterior cruciate ligament reconstruction as presently performed lacks instruments for precisely positioning a guide wire on the femur at a site anatomically equivalent to the anterior cruciate ligament to allow a femoral bone tunnel formed substantially coaxially or concentrically along the guide wire to be optimally, isometrically positioned.

SUMMARY OF THE INVENTION

Accordingly, it is a primary object of the present invention to overcome the above-mentioned disadvantages of femoral guides and methods of forming bone tunnels.

Another object of the present invention is to provide a guide for precisely positioning a guide wire on a bone surface in relation to a reference edge on the bone surface engaged by the guide.

A further object of the present invention is to provide a femoral guide for precisely positioning a guide wire in the femur such that a bone tunnel formed along the guide wire has a longitudinal axis substantially aligned with the anatomic center of attachment of the cruciate ligament, It is also an object of the present invention to provide a guide having a tongue for engaging an edge on a bone surface to position a guide wire inserted through the guide on the bone surface such that a longitudinal axis of a tunnel formed substantially concentrically along the guide wire is a predetermined distance from the edge.

Yet another object of the present invention is to provide a femoral guide having a tongue and a lumen having a longitudinal axis disposed a predetermined distance from the tongue such that a guide wire inserted in the lumen has a longitudinal axis disposed substantially the predetermined distance from the tongue, A still further object of the present invention is to provide a femoral guide for precisely positioning a guide wire on the femur such that a bone tunnel formed along the guide wire has a longitudinal axis approximately 6–7 millimeters anterior to a posterior edge or "over-the-top ridge" of a notch on the femoral condyle, An additional object of the present invention is to provide a guide having a stylus for being driven into the bone to stabilize the guide during insertion of a guide wire into the bone along the guide, Furthermore, it is an object of the present invention to provide a method of precisely forming bone tunnels in a joint of the body endoscopically with a guide inserted at the joint from a portal of minimal size to position a guide wire on a surface of a bone of the joint such that the guide wire is a predetermined distance from a reference edge on the bone surface engaged by the guide allowing the guide wire to be driven into the bone for forming a bone tunnel along the guide wire.

Another object of the present invention is to provide a method of forming bone tunnels in a bone of a joint of the body endoscopically with a guide inserted at the joint from a portal of minimal size and including positioning a tongue of the guide against an edge of a bone surface of the bone such that a guide wire inserted through a lumen of the guide is positioned on the bone surface a distance from the edge that is substantially equal to the distance from the tongue to a longitudinal axis of the lumen.

It is also an object of the present invention to provide a method of forming a femoral bone tunnel in arthroscopic cruciate ligament reconstruction of the knee including the steps of inserting a femoral guide through a tibial bone tunnel from an arthroscopic size portal, positioning a tongue of the femoral guide against a posterior edge of a surface of the femoral condyle, inserting a guide wire through a lumen of the femoral guide to contact the surface of the femoral condyle and driving the guide wire into the femur such that a bone tunnel formed substantially concentrically or coaxially along the guide wire has a longitudinal axis spaced from the reference edge a distance substantially equal to the distance from the tongue to a longitudinal axis of the lumen.

Yet another object of the present invention is to provide a method of arthroscopic anterior cruciate ligament reconstruction of the knee including forming a closed or open end femoral bone tunnel in the femur along a guide wire precisely positioned by a femoral guide inserted through a tibial bone tunnel from an anterolateral or anteromedial portal such that a longitudinal axis of the femoral bone tunnel is disposed 6–7 millimeters anterior to a posterior edge or "over-the-top ridge" of a notch on the femoral condyle.

Some of the advantages of the present invention are that accurate, isometric positioning of tibial and femoral bone tunnels in arthroscopic cruciate ligament reconstruction is enhanced, the time required to perform arthroscopic anterior cruciate ligament reconstruction is reduced, error in forming bone tunnels in arthroscopic cruciate ligament reconstruction is minimized, femoral bone tunnels can readily be located high in a notch formed in the femur, the use of blind, or closed-end, femoral bone tunnels as well as open-end femoral bone tunnels in arthroscopic anterior cruciate ligament reconstruction is permitted, the creation of a trough and not a tunnel when forming femoral bone tunnels is avoided, a cortical margin that is neither too wide nor too narrow is insured, tunnel placement can be verified prior to tunnel formation, the femoral isometric point can be accurately identified, the need for surgeons to estimate the position of drills and reamers when forming femoral bone tunnels along guide wires is eliminated, anteromedial and anterolateral portals can be used for inserting guide wires in arthroscopic anterior cruciate ligament reconstruction, the size of portals used in arthroscopic cruciate ligament reconstruction can be minimized, the femoral guide according to the present invention is streamlined in structure, right and left knee compatible and can be sterilized for repeated use, the tip of a guide wire positioned by the femoral guide on a bone surface can be viewed endoscopically, a footprint can be created on a bone surface as guided by a guide wire positioned by the femoral guide and examined prior to forming a bone tunnel allowing adjustments to be made if necessary, the femoral guide is designed to be accommodated in portals of very small size and the configuration of the femoral guide facilitates manipulation and maneuverability at the knee joint as well as arthroscopic visualization of the knee.

Accordingly, these and other objects and advantages are obtained with the present invention as characterized in a femoral guide including an elongate body having a distal end, a proximal end and a longitudinal lumen for receiving a guide wire and a handle mounting the proximal end of the body. The body includes a cylindrical member and a tip extending angularly, distally from the cylindrical member. The lumen extends through the cylindrical member from the proximal end toward the distal end, the lumen terminating distally at an opening on an arcuate surface of the tip, the opening being disposed proximally of the distal end. The lumen has a diameter sized to closely receive the outer diameter of a guide wire inserted through the femoral guide such that a longitudinal axis of the guide wire is substantially aligned with a longitudinal axis of the lumen, and the opening of the lumen allows the guide wire to protrude distally from the body to contact a bone surface. The arcuate surface of the tip terminates distally at an end wall at the distal end, and a tongue protrudes distally from the end wall and, therefore, the distal end, of the body. The tongue has a surface for engaging a reference edge on a surface of the bone, and the surface of the tongue is disposed a predetermined distance from the longitudinal axis of the lumen such that a guide wire inserted through the lumen will be positioned in contact with the bone surface a distance from the edge that is substantially equal to the predetermined distance. A stylus protrudes from the end wall in the same direction as the tongue allowing the stylus to be driven through the bone surface and into the bone with the bone surface abutting the end wall and the tongue engaging the reference edge. The guide wire can be driven into the bone along the lumen, and the femoral guide can be removed from the guide wire allowing an instrument, such as a cannulated drill or reamer, to be mounted on the guide wire with the guide wire extending through the cannulation to drill a tunnel in the bone substantially concentrically or coaxially along the guide wire such that a longitudinal axis of the tunnel is disposed from the reference edge substantially the predetermined distance. A method of forming bone tunnels endoscopically, or arthroscopically, in joints of the body such as the knee includes the steps of inserting the femoral guide at the joint through a portal of minimal size, positioning a tongue of the femoral guide in engagement with a reference edge on a surface of a bone of the joint, inserting a guide wire through a lumen of the femoral guide and contacting the bone surface with the guide wire at a location spaced from the edge a distance substantially equal to the distance from the tongue to a longitudinal axis of the lumen, driving the guide wire into the bone through the lumen and forming a bone tunnel in the bone substantially concentrically or coaxially along the guide wire.

DESCRIPTION OF THE PREFERRED EMBODIMENTS

Figure 1:
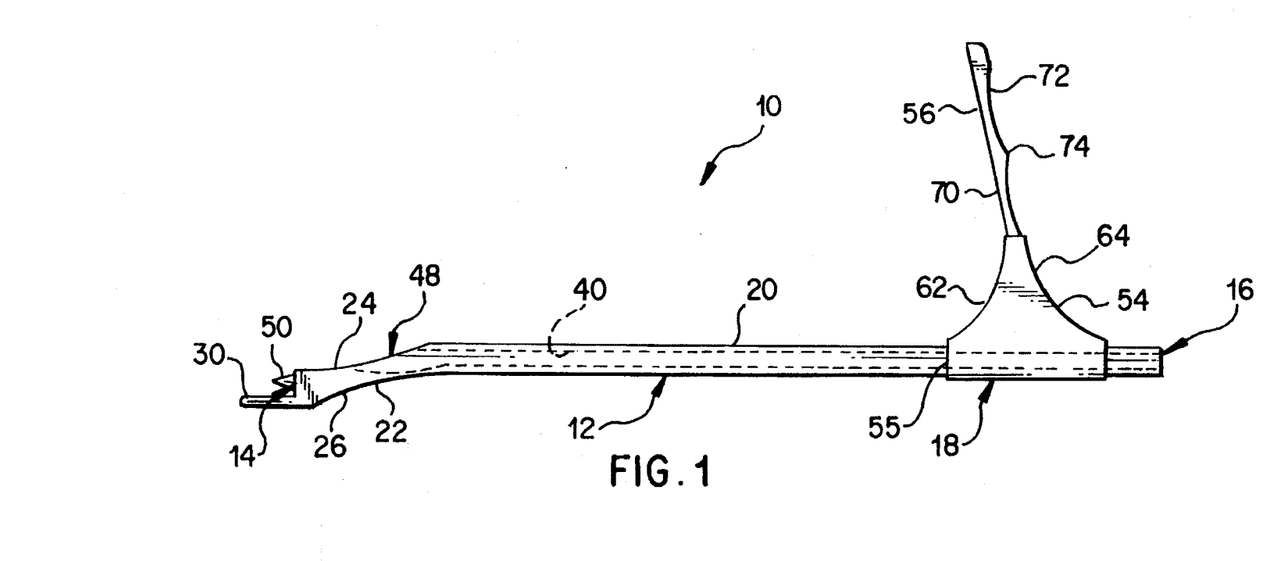
FIG. 1 is a side view of a femoral guide according to the present invention.
Figure 3:
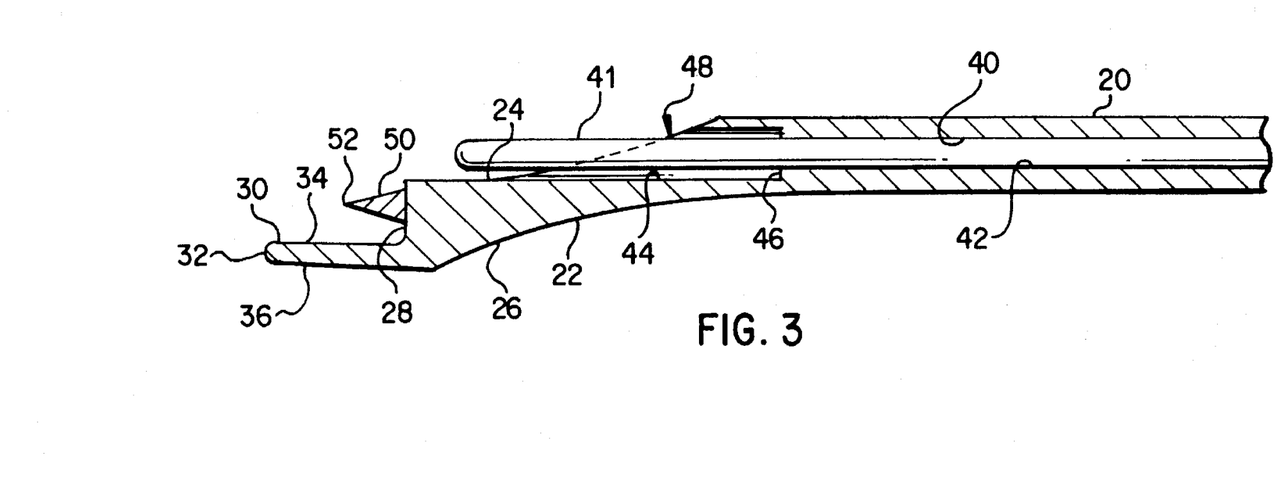
FIG. 3 is an enlarged, broken side view, partly in section, of the femoral guide of FIG. 1.
Figure 4:
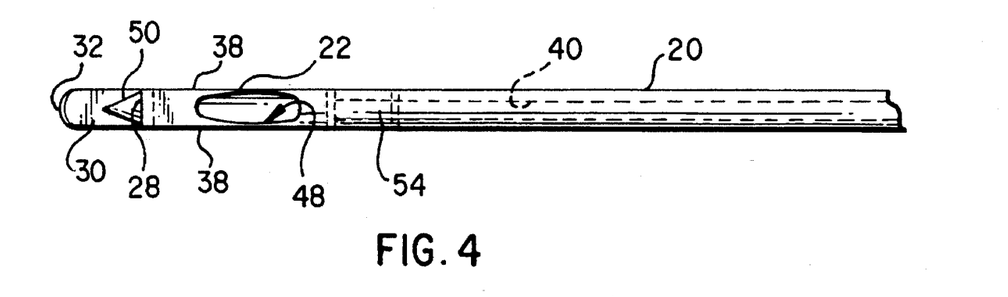
FIG. 4 is a broken top view of the femoral guide of FIG. 1.

A femoral guide according to the present invention is shown at 10 in FIG. 1 and includes a body or probe 12 having a distal end 14, a proximal end 16 and a longitudinal axis and a handle 18 mounting the proximal end 16 of the body 12. The body 12 is preferably made of stainless steel and includes an elongate, cylindrical member or tube 20 terminating proximally at proximal end 16 and a tip 22 distally joined to the cylindrical member 20, the cylindrical member 20 having a longitudinal axis coaxially aligned with the longitudinal axis of the body 12. The tip 22 extends angularly, distally from the cylindrical member 20 and includes an arcuate surface 24 extending distally from a wall of the cylindrical member 20 with an inward curvature and an opposed arcuate surface 26 extending distally with an inward curvature from a wall of the cylindrical member 20. The arcuate surface 24 terminates distally at an end wall 28 at the distal end 14, the end wall 28 having a planar surface disposed in a plane transverse and perpendicular to the longitudinal axis of the body 12 as shown in FIG. 3. A tongue 30 protrudes or extends distally from the end wall 28 and, therefore, the distal end 14, in a direction parallel with the longitudinal axis of the body 12, the tongue 30 terminating distally at an arcuate segment 32 as shown in FIG. 4. The tongue 30 is of generally uniform width and thickness and has a planar surface 34 extending perpendicularly from the end wall 28 to the arcuate segment 32 parallel with and offset from the longitudinal axis of the body and an opposed planar surface 36 joined to arcuate surface 26 and extending from the arcuate surface 26 to the arcuate segment 32 parallel with the upper surface 34. A pair of opposing, parallel side walls 38 having planar surfaces laterally, equidistantly disposed with the longitudinal axis of the body 12 join the arcuate surfaces 24 and 26, the end wall 28 and the tongue 30 with the side walls 38 merging with the cylindrical wall of the body 12 as shown in FIGS. 3 and 4. A longitudinal passage or lumen 40 extends through the body 12, the lumen 40 having a diameter sized to closely receive the outer diameter of a guide wire or pin 41 as shown in FIG. 3 and as will be explained in greater detail below, and a longitudinal axis coaxially aligned with the longitudinal axis of the body 12 such that the longitudinal axis of the lumen is spaced from the upper surface 34 of the tongue 30 by a predetermined distance. The lumen 40 includes a first diameter section 42 in cylindrical member 20 extending from the proximal end 16 in a distal direction and a second, relatively larger diameter section 44 coaxially aligned with the first diameter section 42 and distally joined to the first diameter section 42 within the cylindrical member 20 at an internal, annular shoulder 46, the second diameter section 44 extending distally from the shoulder 46 through the tip 22 to an opening 48 on the arcuate surface 24 that is generally oval or elliptical in configuration when viewed from above as shown in FIG. 4 with the opening 48 being disposed proximally of the end wall 28 and, therefore, the distal end 14. A stylus 50 having a sharp point or tip 52 protrudes distally from the end wall 28 in the same direction as the tongue 30, the stylus 50 having a generally conical configuration with the point 52 at the apex of the conical stylus and an axis of the stylus through the apex being parallel with the upper surface 34 of the tongue 30 such that the stylus can be driven into bone with the end wall 28 abutting a surface of the bone and an edge of the bone surface engaged by the upper surface 34 of the tongue 30 as will be explained further below.

The body 12 can be of integral, unitary construction, or the body 12 can be formed of multiple pieces joined at junctions, such as shown by junction 54 in FIG. 4, by techniques such as welding. Where the body is formed of multiple parts or pieces, it is preferred that the junction 54 be disposed at least 0.250 inches proximally of the shoulder 46. The tip 22 can be formed as a single piece of unitary, integral construction or the tip 22 can be formed of multiple pieces joined by techniques such as welding allowing the stylus 50 and the tongue 30 to be formed separately from the body 12. The body 12 can have various configurations and arrangements of parts providing a lumen sized to closely receive the outer diameter of a guide wire or pin and a tongue protruding distally from the body and having a surface for engaging an edge of a bone surface to position a longitudinal axis of a guide wire received in the lumen on the bone surface a distance from the edge that is substantially equal to the distance from the surface of the tongue to the longitudinal axis of the lumen. Accordingly, it will be appreciated that the lumen 40 need not be coaxially aligned with the body 12, and that the longitudinal axis of the lumen 40 can be offset from the longitudinal axis of the body 12. Depending on the configuration of the bone surface and the edge of the bone surface to be engaged by the tongue, the upper surface of the tongue need not be parallel to the longitudinal axis of the lumen and the end wall need not be perpendicular thereto. Accordingly, it will be appreciated that the tongue and end wall can have various configurations and that the tongue can be angled and non-parallel to the end wall and the longitudinal axis of the lumen. The stylus 50 can have various configurations and can be assembled on the body 12 at various locations to allow the stylus to be driven into bone with an edge of a bone surface engaged by the tongue 30 to secure and stabilize the femoral guide prior to inserting a guide wire through the lumen and when driving the guide wire into bone. According to a preferred embodiment of the femoral guide 10, the diameter of the first diameter section 42 is substantially 0.099 inches to receive a guide wire or pin having an outer diameter of 0.0985 inches, the distance from the upper surface 34 to the longitudinal axis of the lumen 40 is substantially 0.276 inches such that a bone tunnel formed substantially concentrically or coaxially along a guide wire positioned through the lumen of the femoral guide will have a longitudinal axis disposed 6–7 millimeters from the edge of the bone surface engaged by the tongue 30. The length of tongue 30 from end wall 28 to arcuate segment 32 is substantially 0.375 inches, the length of stylus 50 from end wall 28 to point 52 is substantially 0.155 inches, the radius of curvature for arcuate surface 24 measured from a point 3.00 inches from the lower surface 36 and 0.23 inches proximally from arcuate segment 32 looking at FIG. 3 is substantially 2.78 inches, the radius of curvature for arcuate segment 26 measured from a point 2.40 inches from the lower surface 36 and 1.56 inches proximally from the arcuate segment 32 looking at FIG. 3 is substantially 2.65 inches, the outer diameter of cylindrical member 20 is substantially 0.190 inches, the distance between the side walls 38 is substantially 0.150 inches and the overall length of the body 12 from arcuate segment 32 to the proximal end 16 is substantially 6.00 inches. It will be appreciated that the dimensions of the femoral guide can depart from those described here as illustrative and that the femoral guide 10 can have various dimensions and configurations allowing the femoral guide to be inserted through portals of minimal size and to be manipulated within close confines of joints in the body.

Figure 2:
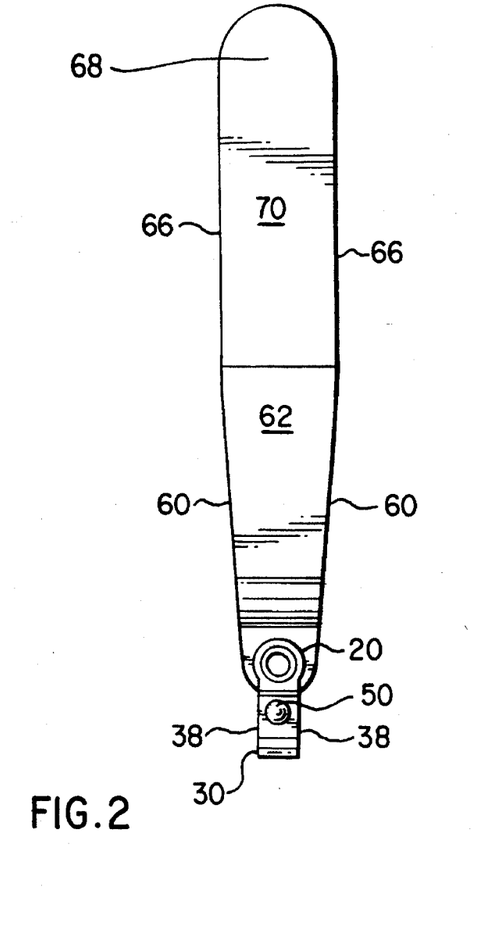
FIG. 2 is a front view of the femoral guide of FIG. 1.

The handle 18 is preferably made of stainless steel and includes a mounting section 54 having a longitudinal, cylindrical passage 55 therein with a diameter sized to closely receive the outer diameter of the cylindrical member 20 of body 12 and a gripping section 58 extending angularly outwardly from the mounting section 54. The mounting section 54 has a pair of opposing side walls 60 defining a width that tapers in the direction of the cylindrical passage 55 as shown in FIG. 2 and a pair of curved forward and rearward walls 62 and 64, respectively, joining the side walls 60 as shown in FIG. 1. As shown in FIG. 1, the forward and rearward walls 62 and 64 curve toward each other such that the length of the handle tapers from near the cylindrical passage 55 to the gripping section 58. The gripping section 58 includes a pair of side walls 66 joined to the side wall 60 and terminating at a radial wall 68 as shown in FIG. 2, and forward and rearward walls 70 and 72, respectively, joining the side walls 66 as shown in FIG. 1. The forward and rearward walls 70 and 72 are joined, respectively, to the forward and rearward walls 62 and 64 of the mounting section 54. Ridges 74 are provided on the rearward wall 72 of the gripping section 58, the ridges 74 extending transverse to the side walls 66 to facilitate grasping of the handle 18 during use. Indicia can be provided on the side walls 60 of the mounting section or at any other suitable location on the handle 18 to identify the distance from the upper surface 34 of tongue 30 to the longitudinal axis of the lumen 40. The cylindrical member 20 of the body 12 is concentrically mounted in the passage 55 of the handle 18 with the proximal end 16 of the body 12 extending proximally of the mounting section 54 a short distance and, preferably, 0.375 inches, as shown in FIG. 1., and the gripping section 58 is disposed diametrically opposite the tongue 30. The body 12 can be secured to handle 18 by techniques such as welding allowing the femoral guide 10 to be sterilized for repeated use utilizing known sterilization procedures. With the body 12 assembled with the handle 18, the gripping section 58 extends angularly, distally in a direction outwardly from the longitudinal axis of the body 12 such that the handle section 58 is disposed at an acute angle with the longitudinal axis of the body 12 for engagement in an inverted position. It will be appreciated that the handle 18 can have various structural configurations to mount the body 12 and provide a gripping section permitting the femoral guide 10 to be grasped and held conveniently, from externally of the body, and to position the tip 22 in the body via a portal of minimal size.

According to a method of operation for the guide 10 in precisely forming bone tunnels in a bone of a joint endoscopically, the femoral guide 10 is inserted at a joint in the body through a portal of minimal size formed in tissue adjacent the joint with the joint being visualized endoscopically. With the handle 18 manually grasped and held in an inverted position externally of the body, the tip 22 is manipulated to position the upper surface 34 of the tongue 30 against an edge of a bone surface that is to have a tunnel entry thereon. With the edge of the bone surface abutting the upper surface 34 of the tongue 30, the longitudinal axis of the lumen 40 will be spaced from the edge a distance that is equal to the distance from the upper surface 34 to the longitudinal axis of the lumen 40. The guide 10 is then driven toward the bone surface such that the sharp point 52 of the stylus 50 enters the bone surface and secures and stabilizes the femoral guide. A guide wire or pin, such as guide wire 41 shown in FIG. 3, is inserted in the lumen 40 from the proximal end 16 of the guide 10 externally of the body. The guide wire 41 will exit the lumen 40 through the opening 48 and, by moving the guide wire 41 toward the bone surface, a tip of the guide wire 41 will contact the bone surface at a point that is spaced from the edge a distance substantially equal to the distance from the upper surface 34 to the longitudinal axis of the lumen 40. The curvature of the arcuate surface 24 allows the tip of the guide wire 41 to be seen endoscopically. An end of the guide wire 41 protruding from the proximal end 16 is coupled, externally of the body, with a tool or instrument for drilling the guide wire in bone, and the guide wire is drilled a desired depth into the bone. The guide 10 is then removed from the guide wire through the portal and a tunneling instrument, such as a drill or reamer, having a central cannulation is mounted on the guide wire 41 externally of the body with the guide wire extending through the cannulation. The tunneling instrument is inserted at the joint through the portal and, with the instrument guided by the guide wire 41, a bone tunnel is formed substantially concentrically or coaxially along the guide wire 41 in the bone to a desired depth such that a longitudinal axis of the bone tunnel is located from the edge a distance substantially equal to the distance from the upper surface 34 to the longitudinal axis of the lumen 40. Accordingly, the guide 10 according to the present invention allows bone tunnels to be formed in bone along guide wires with entry points of the bone tunnels located on surfaces of the bone by positioning the guide wires with the guide at the centers of the tunnel entry points such that the tunnel entry points are precisely located on the bone surfaces in relation to reference points or edges on the bone surfaces that can be engaged by the tongue of the guide.

Figure 5:
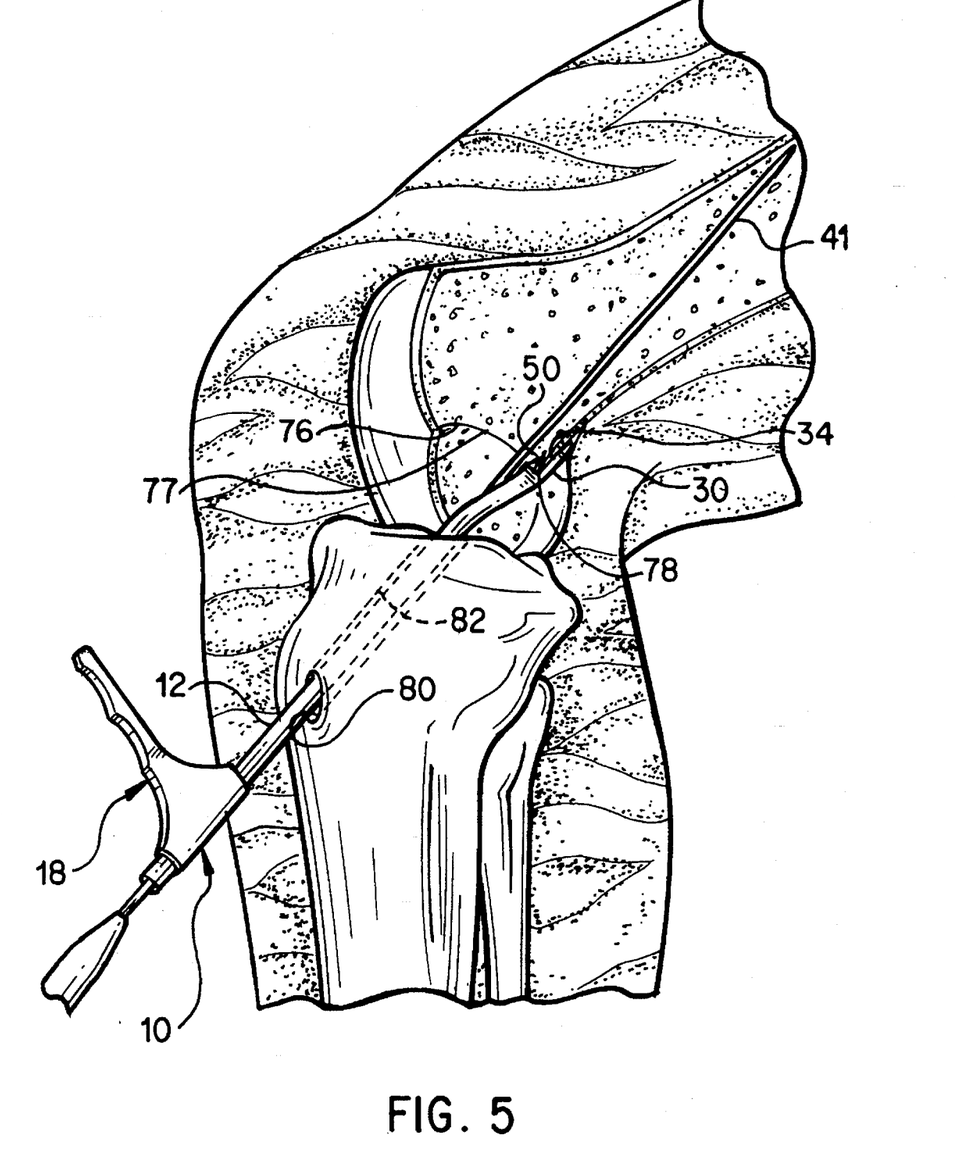
FIG. 5 is a perspective view of a knee showing the femoral guide of FIG. 1 inserting a guide wire in the femur from an anteromedial portal.

The femoral guide 10 according to the present invention is useful in various diverse types of surgical procedures involving the need to precisely position and form bone tunnels in bone endoscopically and, in particular, the femoral guide 10 is useful in ligament reconstruction in joints of the body and, especially, the knee. The femoral guide 10 can be used in reconstructing various diverse types of ligaments and, when used to reconstruct ligaments of the knee, the femoral guide 10 is particularly useful in forming bone tunnels arthroscopically when reconstructing the anterior cruciate ligament of the knee. According to a method of arthroscopic anterior cruciate ligament reconstruction of the knee, a portal of minimal size is formed in tissue adjacent the knee to access the knee joint with the knee being visualized with an arthroscope. A diagnostic arthroscopy can be performed prior to anterior cruciate ligament reconstruction without having to commit to an anterior cruciate ligament reconstruction unless confirmed by the arthroscopic findings. The portal should be placed anteromedial or anterolateral on the knee and, preferably, the portal is placed medially on the knee as a portal placed too high can result in too steep an angle for the tibial bone tunnel while a portal placed too low can interfere with the meniscus. The portal should be placed just superior to the medial meniscus and must not penetrate any portion of the patellar tendon. Instruments are inserted through the portal to perform any necessary procedures such as meniscectomy, minuscal repair, removal of loose bodies, and debridement of anterior cruciate ligament tears. An instrument is inserted through the portal to perform a notchplasty resulting in a notch 76, as shown in FIG. 5, on the femoral condyle, the notch 76 being approximately 2 centimeters in width and adequately posterior to include the extreme posterolateral femoral cortex and having a surface 77 terminating at a posterior edge or "over-the-top" ridge 78. Where an autogenous graft ligament is utilized, a graft having bone blocks at its ends is harvested from the patellar tendon through vertical incisions, i.e., an anteromedial incision or portal beginning 1 centimeter medial to the tibial tubercle and 2 centimeters distally to the joint line and being 2.5 centimeters in length and a patellar incision 2.5 centimeters in length and beginning at the distal pole of the patella and extending proximal over the midline of the patella. A guide wire or pin is placed at the anatomic center of the tibial tunnel entry on the tibia via an anterolateral portal or the anteromedial portal 80 previously used to harvest the graft. An instrument such as a drill or reamer having a cannulation is mounted on the guide wire with the guide wire extending through the cannulation, and a tunnel 82 is drilled in the tibia substantially concentrically or coaxially along the guide wire at a site anatomically equivalent to the anterior cruciate ligament. The drill or reamer and the guide wire are removed from the tibia and, with the knee at an angle of 30° to 45°, the femoral guide 10 is introduced through the tibial bone tunnel 82 from the anteromedial or anterolateral portal 80, and the femoral guide 10 is advanced across the knee joint with the handle 18 held externally of the body. The tongue 30 of the femoral guide 10 is positioned against the posterior edge or ridge 78 and, once positioned, the femoral guide 10 is moved toward the surface 77 to drive the stylus 50 through the surface 77 and into the femur thusly securing or stabilizing the femoral guide 10. A guide wire 41 is inserted through the lumen of the femoral guide from externally of the body such that a tip of the guide wire protruding through the opening 48 contacts the surface 77 to establish a longitudinal axis or center for an entry point of a tunnel to be formed in the femur along the guide wire 41, the arcuate surface 24 allowing the tip of the guide wire 41 to be seen arthroscopically. A desired position for the femoral bone tunnel is high in the notch 76 with a longitudinal axis or center of the femoral bone tunnel located approximately 6–7 millimeters anterior to the edge or ridge 78, and the distance from the upper surface 34 of the tongue 30 to the longitudinal axis of the lumen 40 results in the guide wire 41 being placed at the desired position on the surface 77. An end of the guide wire 41 protruding from the proximal end 16 of the femoral guide 10 is coupled with an instrument for drilling the guide wire 41 in bone, and the guide wire 41 is drilled into the femur as shown in FIG. 5. The guide wire is drilled into the femur a depth of approximately 3–4 centimeters for a blind, or closed end, femoral bone tunnel and, for an open end femoral bone tunnel, the guide wire 41 is drilled into the femur until it exits the lateral femoral cortex but not through the skin. The femoral guide 10 is backed out of the femur and removed from the knee through the portal 80, and an instrument for forming a bone tunnel, such as a drill or reamer, having a cannulation therein is mounted on the guide wire 41 with the guide wire extending through the cannulation. The drill or reamer is inserted through the portal 80 along the guide wire, and a footprint of the drill or reamer is created on the surface 77 and examined arthroscopically to insure accurate positioning of the femoral bone tunnel entry point. The width of the posterior cortex remaining should be approximately 1–2 millimeters, the posterolateral femoral cortex must be adequately identified and the femoral bone tunnel should be as far posterior as possible while still allowing a tunnel and not a trough. If the cortical margin is too wide or too narrow, the guide wire 41 may be reinserted and another footprint made and examined until accurate placement of the bone tunnel is confirmed. Once the entry point for the femoral bone tunnel has been properly placed, the femoral bone tunnel is drilled along the guide wire and, for a blind tunnel, the tunnel is drilled slightly deeper than the length of the bone block intended for fixation in the femoral bone tunnel and, for an open tunnel, the tunnel is drilled through the lateral femoral cortex. The drill or reamer and the guide wire 41 are removed through the portal 80, and the autogenous ligament or a prosthetic ligament is inserted through the tibial bone tunnel and across the knee joint with a bone block disposed in each of the bone tunnels. Interference bone fixation screws are then inserted in the tibial and femoral bone tunnels laterally between the bone blocks and walls of the bone tunnels in directions parallel with longitudinal axes of the bone tunnels to fixate the ligament.

Accordingly, the femoral guide and methods of forming bone tunnels endoscopically according to the present invention allow bone tunnels to be precisely formed endoscopically in bone along guide wires by positioning the guide wires such that longitudinal axes of the bone tunnels formed substantially concentrically or coaxially along the guide wires are spaced from reference edges on the bone a predetermined distance. The femoral guide of the present invention allows femoral bone tunnels to be precisely positioned in arthroscopic cruciate ligament reconstruction at sites anatomically equivalent to the cruciate ligament to insure accurate graft or prosthetic ligament placement and isometricity. The femoral guide permits the use of small size portals in arthroscopic cruciate ligament reconstruction and is designed to facilitate manipulation and maneuverability at the knee joint. The femoral guide facilitates arthroscopic viewing of the tip of the guide wire on the femoral condyle and examination of the footprint created prior to forming the femoral bone tunnel. The femoral guide and the methods of forming bone tunnels according to the present invention allow guide wires to be inserted at the knee from anterolateral and anteromedial portals and reduce the number of portals required in arthroscopic cruciate ligament reconstruction of the knee. By precisely positioning a guide wire a predetermined distance from an edge on a bone surface, the femoral guide and methods of forming bone tunnels according to the present invention avoid errors in placing bone tunnels and eliminate the need for surgeons to estimate where to put instruments, such as drills or reamers, when forming bone tunnels. The tongue of the femoral guide according to the present invention allows an edge, a ridge or some other structure of bone to be used as a reference in forming bone tunnels such that longitudinal axes of bone tunnels formed along guide wires positioned via the femoral guide will be located a predetermined distance from the reference. The stylus of the femoral guide enhances accuracy and precision in forming bone tunnels by securing or stabilizing the femoral guide relative to the bone prior to drilling the guide wire.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A guide for positioning a guide wire on a bone having a bone surface with an edge to allow a tunnel to be formed in the bone along the guide wire including:
   an elongate body having a distal end and a proximal end, said body including a cylindrical member and an arcuate surface extending distally from said cylindrical member and terminating distally at an end wall at said distal end, said end wall being disposed in a plane;
   a lumen in said body for receiving a guide wire and having a longitudinal axis perpendicular to the plane in which said end wall is disposed, said lumen extending from said proximal end to an opening formed on said arcuate surface for allowing the guide wire to protrude from said body to contact the bone surface; and
   a tongue on said body having a surface spaced from said longitudinal axis and protruding distally from said end wall beyond said opening for engaging the edge of the bone surface whereby a guide wire protruding from said body contacts the bone surface at a location spaced from the edge a distance substantially equal to the distance that said surface of said tongue is spaced from said longitudinal axis of said lumen.

2. A guide as recited in claim 1 wherein said surface of said tongue is parallel with said longitudinal axis of said lumen.

3. A guide as recited in claim 2 wherein said body includes an arcuate surface joining said tongue to said cylindrical member and said arcuate surfaces have an inward curvature.

4. A guide as recited in claim 3 wherein said body includes a pair of parallel walls joining said arcuate surfaces, said end wall, said tongue and said cylindrical member.

5. A guide as recited in claim 4 wherein said lumen has a diameter sized to closely receive an outer diameter of the guide wire.

6. A guide as recited in claim 5 wherein said body includes a longitudinal axis and said lumen longitudinal axis is coaxially aligned with said body longitudinal axis.

7. A guide as recited in claim 1 further including a stylus on said end wall for being driven through the bone surface and into the bone to secure said body with said tongue in engagement with the edge of the bone surface.

8. A guide for positioning a guide wire on a bone having a bone surface to allow a tunnel to be formed in the bone substantially concentrically along the guide wire including:
   an elongate body having a distal end and a proximal end, said body including a cylindrical member having said proximal end and a tip extending angularly, distally from said cylindrical member, said tip including an end wall at said distal end and an arcuate surface joining said end wall to said cylindrical member;
   a lumen disposed in said body for receiving a guide wire and having an opening formed in said arcuate surface proximally of said end wall for allowing the guide wire to protrude from said body to contact the bone surface; and
   a stylus protruding in a distal direction from said end wall and having a sharp tip for penetrating bone whereby said stylus can be driven through the bone surface and into the bone to secure said body to the bone to allow a guide wire protruding from said body to be driven into the bone through said lumen.

9. A guide as recited in claim 8 wherein said lumen includes a longitudinal axis and said stylus includes a longitudinal axis parallel with said lumen longitudinal axis.

10. A guide as recited in claim 9 wherein said stylus has a conical configuration.

11. A guide as recited in claim 10 wherein said lumen has a diameter to receive an outer diameter of a guide wire having a longitudinal axis with the longitudinal axis of the guide wire substantially aligned with said longitudinal axis of said lumen.

12. A guide as recited in claim 11 further including a tongue on said body spaced from said longitudinal axis of said lumen for engaging the bone surface at a reference point on the bone surface to position said longitudinal axis of said lumen a distance from the reference point that is the same as the distance from said tongue to said longitudinal axis of said lumen.

* * * * *